US012569619B2

(12) United States Patent
Lee et al.

(10) Patent No.: US 12,569,619 B2
(45) Date of Patent: Mar. 10, 2026

(54) TECHNIQUES FOR DETERMINING AUTOMATED INSULIN DELIVERY DOSAGES

(71) Applicant: Insulet Corporation, Acton, MA (US)

(72) Inventors: Joon Bok Lee, Acton, MA (US); Yibin Zheng, Hartland, WI (US); Steven Cardinali, Tewksbury, MA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 602 days.

(21) Appl. No.: 17/027,191

(22) Filed: Sep. 21, 2020

(65) Prior Publication Data

US 2022/0088303 A1 Mar. 24, 2022

(51) Int. Cl.
*A61M 5/172* (2006.01)
*A61B 5/00* (2006.01)
(Continued)

(52) U.S. Cl.
CPC ...... *A61M 5/1723* (2013.01); *A61M 5/16804* (2013.01); *A61B 5/14532* (2013.01);
(Continued)

(58) Field of Classification Search
CPC ............ A61M 5/1723; A61M 5/16804; A61M 2005/14208; A61M 2005/3327;
(Continued)

(56) References Cited

U.S. PATENT DOCUMENTS 303,013 A 8/1884 Horton
2,797,149 A 6/1957 Skeggs
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — William R Carpenter
*Assistant Examiner* — Robert F Allen
(74) *Attorney, Agent, or Firm* — GOODWIN PROCTER LLP

(57) ABSTRACT

Methods and apparatuses for performing an insulin infusion process are described. For example, an apparatus may include at least one memory and logic coupled to the at least one memory. The logic may operate to determine a basal parameter for a patient based on a type 2 diabetes (T2D) multiple daily injection (MDI) information of the patient, the basal parameter indicating a basal infusion rate, determine an additional insulin ($I_{add}$) value based on a mean blood glucose difference ($BG_{diff}$) information associated with the patient, determine an insulin volume to infuse into the patient based on the basal parameter and $I_{add}$, and administer the insulin volume to the patient. Other embodiments are described.

19 Claims, 6 Drawing Sheets

(51) Int. Cl.

| | |
|---|---|
| *A61B 5/145* | (2006.01) |
| *A61K 38/28* | (2006.01) |
| *A61M 5/142* | (2006.01) |
| *A61M 5/168* | (2006.01) |

(52) U.S. Cl.
CPC ............. *A61B 5/7275* (2013.01); *A61K 38/28* (2013.01); *A61M 2005/14208* (2013.01); *A61M 2205/3327* (2013.01); *A61M 2205/50* (2013.01); *A61M 2205/52* (2013.01); *A61M 2230/201* (2013.01)

(58) Field of Classification Search
CPC ...... A61M 2005/52; A61M 2205/3327; A61M 2205/50; A61M 2205/52; A61M 2230/201; G16H 20/17; A61B 5/14532; A61B 5/7275; A61K 38/28
See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |

(56)                    References Cited

U.S. PATENT DOCUMENTS

| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Ebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,140,275 B2 * | 3/2012 | Campbell ......... A61M 5/14244 |
| | | 702/50 |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko et al. |
| 9,579,456 B2 | 2/2017 | Budiman et al. |
| 9,743,224 B2 | 8/2017 | San Vicente et al. |
| 9,782,540 B2 * | 10/2017 | Lebel ................ A61M 5/14276 |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |

(56) References Cited

U.S. PATENT DOCUMENTS

| | | | |
|---|---|---|---|
| 10,583,250 | B2 | 3/2020 | Mazlish et al. |
| 10,737,024 | B2 | 8/2020 | Schmid |
| 10,881,792 | B2* | 1/2021 | Mazlish ............ A61M 5/14248 |
| 10,987,468 | B2 | 4/2021 | Mazlish et al. |
| 11,197,964 | B2 | 12/2021 | Sjolund et al. |
| 11,260,169 | B2 | 3/2022 | Estes |
| 2001/0021803 | A1 | 9/2001 | Blank et al. |
| 2001/0034023 | A1 | 10/2001 | Stanton, Jr. et al. |
| 2001/0034502 | A1 | 10/2001 | Moberg et al. |
| 2001/0051377 | A1 | 12/2001 | Hammer et al. |
| 2001/0053895 | A1 | 12/2001 | Vaillancourt |
| 2002/0010401 | A1 | 1/2002 | Bushmakin et al. |
| 2002/0010423 | A1 | 1/2002 | Gross et al. |
| 2002/0016568 | A1 | 2/2002 | Lebel et al. |
| 2002/0040208 | A1 | 4/2002 | Flaherty et al. |
| 2002/0123740 | A1 | 9/2002 | Flaherty et al. |
| 2002/0128543 | A1 | 9/2002 | Leonhardt |
| 2002/0147423 | A1 | 10/2002 | Burbank et al. |
| 2002/0155425 | A1 | 10/2002 | Han et al. |
| 2002/0161288 | A1 | 10/2002 | Shin et al. |
| 2003/0023148 | A1 | 1/2003 | Lorenz et al. |
| 2003/0050621 | A1 | 3/2003 | Ebel et al. |
| 2003/0060692 | A1 | 3/2003 | Ruchti et al. |
| 2003/0086074 | A1 | 5/2003 | Braig et al. |
| 2003/0086075 | A1 | 5/2003 | Braig et al. |
| 2003/0090649 | A1 | 5/2003 | Sterling et al. |
| 2003/0100040 | A1 | 5/2003 | Bonnecaze et al. |
| 2003/0130616 | A1 | 7/2003 | Steil et al. |
| 2003/0135388 | A1 | 7/2003 | Martucci et al. |
| 2003/0144582 | A1 | 7/2003 | Cohen et al. |
| 2003/0163088 | A1* | 8/2003 | Blomquist ............ G16H 20/17 |
| | | | 700/282 |
| 2003/0163097 | A1 | 8/2003 | Fleury et al. |
| 2003/0163223 | A1* | 8/2003 | Blomquist .......... A61M 5/1723 |
| | | | 700/282 |
| 2003/0195404 | A1 | 10/2003 | Knobbe et al. |
| 2003/0208113 | A1 | 11/2003 | Mault et al. |
| 2003/0208154 | A1 | 11/2003 | Close et al. |
| 2003/0212379 | A1 | 11/2003 | Bylund et al. |
| 2003/0216627 | A1 | 11/2003 | Lorenz et al. |
| 2003/0220605 | A1 | 11/2003 | Bowman, Jr. et al. |
| 2004/0010207 | A1 | 1/2004 | Flaherty et al. |
| 2004/0034295 | A1 | 2/2004 | Salganicoff |
| 2004/0045879 | A1 | 3/2004 | Shults et al. |
| 2004/0051368 | A1 | 3/2004 | Caputo et al. |
| 2004/0064259 | A1 | 4/2004 | Haaland et al. |
| 2004/0097796 | A1 | 5/2004 | Berman et al. |
| 2004/0116847 | A1 | 6/2004 | Wall |
| 2004/0122353 | A1 | 6/2004 | Shahmirian et al. |
| 2004/0133166 | A1 | 7/2004 | Moberg et al. |
| 2004/0147034 | A1 | 7/2004 | Gore et al. |
| 2004/0171983 | A1 | 9/2004 | Sparks et al. |
| 2004/0203357 | A1 | 10/2004 | Nassimi |
| 2004/0204868 | A1 | 10/2004 | Maynard et al. |
| 2004/0215492 | A1 | 10/2004 | Choi |
| 2004/0220517 | A1 | 11/2004 | Starkweather et al. |
| 2004/0241736 | A1 | 12/2004 | Hendee et al. |
| 2004/0249308 | A1 | 12/2004 | Forssell |
| 2005/0003470 | A1 | 1/2005 | Nelson et al. |
| 2005/0020980 | A1 | 1/2005 | Inoue et al. |
| 2005/0022274 | A1 | 1/2005 | Campbell et al. |
| 2005/0033148 | A1 | 2/2005 | Haueter et al. |
| 2005/0049179 | A1 | 3/2005 | Davidson et al. |
| 2005/0065464 | A1 | 3/2005 | Talbot et al. |
| 2005/0065465 | A1 | 3/2005 | Lebel et al. |
| 2005/0075624 | A1 | 4/2005 | Miesel |
| 2005/0105095 | A1 | 5/2005 | Pesach et al. |
| 2005/0137573 | A1 | 6/2005 | Mclaughlin |
| 2005/0171503 | A1 | 8/2005 | Van Den Berghe et al. |
| 2005/0182306 | A1 | 8/2005 | Sloan |
| 2005/0192494 | A1 | 9/2005 | Ginsberg |
| 2005/0192557 | A1 | 9/2005 | Brauker et al. |
| 2005/0197621 | A1 | 9/2005 | Poulsen et al. |
| 2005/0203360 | A1 | 9/2005 | Brauker et al. |
| 2005/0203461 | A1 | 9/2005 | Flaherty et al. |
| 2005/0238507 | A1 | 10/2005 | Dilanni et al. |
| 2005/0261660 | A1 | 11/2005 | Choi |
| 2005/0272640 | A1 | 12/2005 | Doyle, III et al. |
| 2005/0277912 | A1 | 12/2005 | John |
| 2006/0009727 | A1 | 1/2006 | OMahony et al. |
| 2006/0079809 | A1 | 4/2006 | Goldberger et al. |
| 2006/0100494 | A1 | 5/2006 | Kroll |
| 2006/0134323 | A1 | 6/2006 | OBrien |
| 2006/0167350 | A1 | 7/2006 | Monfre et al. |
| 2006/0173406 | A1 | 8/2006 | Hayes et al. |
| 2006/0189925 | A1 | 8/2006 | Gable et al. |
| 2006/0189926 | A1 | 8/2006 | Hall et al. |
| 2006/0197015 | A1 | 9/2006 | Sterling et al. |
| 2006/0200070 | A1 | 9/2006 | Callicoat et al. |
| 2006/0204535 | A1 | 9/2006 | Johnson |
| 2006/0229531 | A1 | 10/2006 | Goldberger et al. |
| 2006/0253085 | A1 | 11/2006 | Geismar et al. |
| 2006/0264895 | A1 | 11/2006 | Flanders |
| 2006/0270983 | A1 | 11/2006 | Lord et al. |
| 2006/0276771 | A1 | 12/2006 | Galley et al. |
| 2006/0282290 | A1 | 12/2006 | Flaherty et al. |
| 2007/0016127 | A1 | 1/2007 | Staib et al. |
| 2007/0060796 | A1 | 3/2007 | Kim |
| 2007/0060869 | A1 | 3/2007 | Tolle et al. |
| 2007/0060872 | A1 | 3/2007 | Hall et al. |
| 2007/0078314 | A1* | 4/2007 | Grounsell .............. G16H 20/17 |
| | | | 600/319 |
| 2007/0083160 | A1 | 4/2007 | Hall et al. |
| 2007/0106135 | A1 | 5/2007 | Sloan et al. |
| 2007/0116601 | A1 | 5/2007 | Patton |
| 2007/0118405 | A1 | 5/2007 | Campbell et al. |
| 2007/0129690 | A1 | 6/2007 | Rosenblatt et al. |
| 2007/0142720 | A1 | 6/2007 | Ridder et al. |
| 2007/0173761 | A1 | 7/2007 | Kanderian et al. |
| 2007/0173974 | A1 | 7/2007 | Lin |
| 2007/0179352 | A1 | 8/2007 | Randlov et al. |
| 2007/0191716 | A1 | 8/2007 | Goldberger et al. |
| 2007/0197163 | A1 | 8/2007 | Robertson |
| 2007/0225675 | A1 | 9/2007 | Robinson et al. |
| 2007/0244381 | A1 | 10/2007 | Robinson et al. |
| 2007/0249007 | A1 | 10/2007 | Rosero |
| 2007/0264707 | A1 | 11/2007 | Liederman et al. |
| 2007/0282269 | A1 | 12/2007 | Carter et al. |
| 2007/0287985 | A1 | 12/2007 | Estes et al. |
| 2007/0293843 | A1 | 12/2007 | Ireland et al. |
| 2008/0033272 | A1 | 2/2008 | Gough et al. |
| 2008/0051764 | A1 | 2/2008 | Dent et al. |
| 2008/0058625 | A1 | 3/2008 | McGarraugh et al. |
| 2008/0065050 | A1 | 3/2008 | Sparks et al. |
| 2008/0071157 | A1 | 3/2008 | McGarraugh et al. |
| 2008/0071158 | A1 | 3/2008 | McGarraugh et al. |
| 2008/0078400 | A1 | 4/2008 | Martens et al. |
| 2008/0097289 | A1 | 4/2008 | Steil et al. |
| 2008/0132880 | A1 | 6/2008 | Buchman |
| 2008/0161664 | A1 | 7/2008 | Mastrototaro et al. |
| 2008/0172026 | A1 | 7/2008 | Blomquist |
| 2008/0177165 | A1 | 7/2008 | Blomquist et al. |
| 2008/0188796 | A1 | 8/2008 | Steil et al. |
| 2008/0200838 | A1 | 8/2008 | Goldberger et al. |
| 2008/0206067 | A1 | 8/2008 | De Corral et al. |
| 2008/0208113 | A1 | 8/2008 | Damiano et al. |
| 2008/0214919 | A1 | 9/2008 | Harmon et al. |
| 2008/0228056 | A1 | 9/2008 | Blomquist et al. |
| 2008/0249386 | A1 | 10/2008 | Besterman et al. |
| 2008/0269585 | A1 | 10/2008 | Ginsberg |
| 2008/0269714 | A1 | 10/2008 | Mastrototaro et al. |
| 2008/0269723 | A1 | 10/2008 | Mastrototaro et al. |
| 2008/0287906 | A1 | 11/2008 | Burkholz et al. |
| 2009/0006061 | A1 | 1/2009 | Thukral et al. |
| 2009/0018406 | A1 | 1/2009 | Yodfat et al. |
| 2009/0030398 | A1 | 1/2009 | Yodfat et al. |
| 2009/0036753 | A1 | 2/2009 | King |
| 2009/0043240 | A1 | 2/2009 | Robinson et al. |
| 2009/0054753 | A1 | 2/2009 | Robinson et al. |
| 2009/0069743 | A1 | 3/2009 | Krishnamoorthy et al. |
| 2009/0069745 | A1 | 3/2009 | Estes et al. |
| 2009/0069787 | A1 | 3/2009 | Estes et al. |
| 2009/0099521 | A1 | 4/2009 | Gravesen et al. |
| 2009/0105573 | A1 | 4/2009 | Malecha |

(56) References Cited

U.S. PATENT DOCUMENTS

| | | | |
|---|---|---|---|
| 2009/0131861 A1 | 5/2009 | Braig et al. | |
| 2009/0156922 A1 | 6/2009 | Goldberger et al. | |
| 2009/0156924 A1 | 6/2009 | Shariati et al. | |
| 2009/0163781 A1 | 6/2009 | Say et al. | |
| 2009/0198350 A1 | 8/2009 | Thiele | |
| 2009/0221890 A1 | 9/2009 | Saffer et al. | |
| 2009/0228214 A1 | 9/2009 | Say et al. | |
| 2009/0318791 A1 | 12/2009 | Kaastrup | |
| 2009/0326343 A1 | 12/2009 | Gable et al. | |
| 2010/0017141 A1* | 1/2010 | Campbell | A61M 5/14244 |
| | | | 702/19 |
| 2010/0057042 A1 | 3/2010 | Hayter | |
| 2010/0114026 A1 | 5/2010 | Karratt et al. | |
| 2010/0121170 A1 | 5/2010 | Rule | |
| 2010/0137784 A1 | 6/2010 | Cefai et al. | |
| 2010/0152658 A1 | 6/2010 | Hanson et al. | |
| 2010/0174228 A1 | 7/2010 | Buckingham et al. | |
| 2010/0211003 A1 | 8/2010 | Sundar et al. | |
| 2010/0228110 A1 | 9/2010 | Tsoukalis | |
| 2010/0262117 A1 | 10/2010 | Magni et al. | |
| 2010/0262434 A1 | 10/2010 | Shaya | |
| 2010/0295686 A1 | 11/2010 | Sloan et al. | |
| 2010/0298765 A1 | 11/2010 | Budiman et al. | |
| 2011/0021584 A1 | 1/2011 | Berggren et al. | |
| 2011/0028817 A1 | 2/2011 | Jin et al. | |
| 2011/0054390 A1 | 3/2011 | Searle et al. | |
| 2011/0054399 A1 | 3/2011 | Chong et al. | |
| 2011/0124996 A1 | 5/2011 | Reinke et al. | |
| 2011/0144586 A1 | 6/2011 | Michaud et al. | |
| 2011/0160652 A1 | 6/2011 | Yodfat et al. | |
| 2011/0178472 A1 | 7/2011 | Cabiri | |
| 2011/0190694 A1 | 8/2011 | Lanier, Jr. et al. | |
| 2011/0202005 A1 | 8/2011 | Yodfat et al. | |
| 2011/0218495 A1 | 9/2011 | Remde | |
| 2011/0230833 A1 | 9/2011 | Andman et al. | |
| 2011/0251509 A1 | 10/2011 | Beyhan et al. | |
| 2011/0313680 A1 | 12/2011 | Doyle et al. | |
| 2011/0316562 A1 | 12/2011 | Cefai et al. | |
| 2012/0003935 A1 | 1/2012 | Lydon et al. | |
| 2012/0010594 A1 | 1/2012 | Holt et al. | |
| 2012/0030393 A1 | 2/2012 | Ganesh et al. | |
| 2012/0053556 A1 | 3/2012 | Lee | |
| 2012/0078067 A1 | 3/2012 | Kovatchev et al. | |
| 2012/0078161 A1 | 3/2012 | Masterson et al. | |
| 2012/0078181 A1 | 3/2012 | Smith et al. | |
| 2012/0101451 A1 | 4/2012 | Boit et al. | |
| 2012/0123234 A1* | 5/2012 | Atlas | A61B 5/7264 |
| | | | 600/365 |
| 2012/0136336 A1 | 5/2012 | Mastrototaro et al. | |
| 2012/0190955 A1 | 7/2012 | Rao et al. | |
| 2012/0203085 A1 | 8/2012 | Rebec | |
| 2012/0203178 A1 | 8/2012 | Tverskoy | |
| 2012/0215087 A1 | 8/2012 | Cobelli et al. | |
| 2012/0225134 A1 | 9/2012 | Komorowski | |
| 2012/0226259 A1 | 9/2012 | Yodfat et al. | |
| 2012/0232520 A1 | 9/2012 | Sloan et al. | |
| 2012/0238851 A1 | 9/2012 | Kamen et al. | |
| 2012/0246106 A1* | 9/2012 | Atlas | G16H 50/20 |
| | | | 700/282 |
| 2012/0271655 A1 | 10/2012 | Knobel et al. | |
| 2012/0277668 A1 | 11/2012 | Chawla et al. | |
| 2012/0282111 A1 | 11/2012 | Nip et al. | |
| 2012/0295550 A1 | 11/2012 | Wilson et al. | |
| 2013/0030358 A1 | 1/2013 | Yodfat et al. | |
| 2013/0158503 A1 | 6/2013 | Kanderian, Jr. et al. | |
| 2013/0178791 A1 | 7/2013 | Javitt | |
| 2013/0231642 A1 | 9/2013 | Doyle et al. | |
| 2013/0253472 A1 | 9/2013 | Cabiri | |
| 2013/0261406 A1 | 10/2013 | Rebec et al. | |
| 2013/0296823 A1 | 11/2013 | Melker et al. | |
| 2013/0317753 A1 | 11/2013 | Kamen et al. | |
| 2013/0338576 A1 | 12/2013 | OConnor et al. | |
| 2014/0005633 A1 | 1/2014 | Finan | |
| 2014/0066886 A1 | 3/2014 | Roy et al. | |
| 2014/0074033 A1 | 3/2014 | Sonderegger et al. | |
| 2014/0121635 A1 | 5/2014 | Hayter | |
| 2014/0128839 A1 | 5/2014 | Dilanni et al. | |
| 2014/0135880 A1 | 5/2014 | Baumgartner et al. | |
| 2014/0146202 A1 | 5/2014 | Boss et al. | |
| 2014/0180203 A1 | 6/2014 | Budiman et al. | |
| 2014/0180240 A1 | 6/2014 | Finan et al. | |
| 2014/0200426 A1 | 7/2014 | Taub et al. | |
| 2014/0200559 A1 | 7/2014 | Doyle et al. | |
| 2014/0230021 A1 | 8/2014 | Birthwhistle et al. | |
| 2014/0276554 A1 | 9/2014 | Finan et al. | |
| 2014/0276556 A1 | 9/2014 | Saint et al. | |
| 2014/0278123 A1 | 9/2014 | Prodhom et al. | |
| 2014/0316379 A1 | 10/2014 | Sonderegger et al. | |
| 2014/0325065 A1 | 10/2014 | Birtwhistle et al. | |
| 2015/0018633 A1 | 1/2015 | Kovachev et al. | |
| 2015/0025329 A1 | 1/2015 | Amarasingham et al. | |
| 2015/0025495 A1 | 1/2015 | Peyser | |
| 2015/0120317 A1 | 4/2015 | Mayou et al. | |
| 2015/0134265 A1 | 5/2015 | Kohlbrecher et al. | |
| 2015/0165119 A1 | 6/2015 | Palerm et al. | |
| 2015/0173674 A1 | 6/2015 | Hayes et al. | |
| 2015/0213217 A1 | 7/2015 | Amarasingham et al. | |
| 2015/0217052 A1 | 8/2015 | Keenan et al. | |
| 2015/0217053 A1 | 8/2015 | Booth et al. | |
| 2015/0265767 A1 | 9/2015 | Vazquez et al. | |
| 2015/0306314 A1 | 10/2015 | Doyle et al. | |
| 2015/0351671 A1 | 12/2015 | Vanslyke et al. | |
| 2015/0366945 A1 | 12/2015 | Greene | |
| 2016/0015891 A1 | 1/2016 | Papiorek | |
| 2016/0038673 A1 | 2/2016 | Morales | |
| 2016/0038689 A1 | 2/2016 | Lee et al. | |
| 2016/0051749 A1 | 2/2016 | Istoc | |
| 2016/0082187 A1 | 3/2016 | Schaible et al. | |
| 2016/0089494 A1 | 3/2016 | Guerrini | |
| 2016/0117481 A1* | 4/2016 | Booth | G16H 10/40 |
| | | | 604/502 |
| 2016/0175520 A1 | 6/2016 | Palerm et al. | |
| 2016/0228641 A1 | 8/2016 | Gescheit et al. | |
| 2016/0243318 A1 | 8/2016 | Despa et al. | |
| 2016/0256087 A1 | 9/2016 | Doyle et al. | |
| 2016/0287512 A1 | 10/2016 | Cooper et al. | |
| 2016/0302054 A1 | 10/2016 | Kimura et al. | |
| 2016/0331310 A1 | 11/2016 | Kovatchev | |
| 2016/0354543 A1 | 12/2016 | Cinar et al. | |
| 2017/0049386 A1 | 2/2017 | Abraham et al. | |
| 2017/0053101 A1* | 2/2017 | Booth | G16H 70/20 |
| 2017/0143899 A1 | 5/2017 | Gondhalekar et al. | |
| 2017/0143900 A1 | 5/2017 | Rioux et al. | |
| 2017/0156682 A1 | 6/2017 | Doyle et al. | |
| 2017/0173261 A1 | 6/2017 | O'Connor et al. | |
| 2017/0189614 A1* | 7/2017 | Mazlish | A61M 5/1723 |
| 2017/0189625 A1 | 7/2017 | Cirillo et al. | |
| 2017/0220750 A1* | 8/2017 | Davis | G06N 20/00 |
| 2017/0281877 A1 | 10/2017 | Marlin et al. | |
| 2017/0296746 A1 | 10/2017 | Chen et al. | |
| 2017/0311903 A1 | 11/2017 | Davis et al. | |
| 2017/0348482 A1 | 12/2017 | Duke et al. | |
| 2017/0351842 A1* | 12/2017 | Booth | G16H 20/60 |
| 2018/0036495 A1 | 2/2018 | Searle et al. | |
| 2018/0040255 A1 | 2/2018 | Freeman et al. | |
| 2018/0075200 A1 | 3/2018 | Davis et al. | |
| 2018/0075201 A1 | 3/2018 | Davis et al. | |
| 2018/0075202 A1 | 3/2018 | Davis et al. | |
| 2018/0092576 A1 | 4/2018 | Ambrosio et al. | |
| 2018/0126073 A1 | 5/2018 | Wu et al. | |
| 2018/0169334 A1 | 6/2018 | Grosman et al. | |
| 2018/0200434 A1 | 7/2018 | Mazlish et al. | |
| 2018/0200438 A1 | 7/2018 | Mazlish et al. | |
| 2018/0200441 A1 | 7/2018 | Desborough et al. | |
| 2018/0204636 A1 | 7/2018 | Edwards et al. | |
| 2018/0235524 A1* | 8/2018 | Dunn | A61B 5/4836 |
| 2018/0277253 A1 | 9/2018 | Gondhalekar et al. | |
| 2018/0289891 A1 | 10/2018 | Finan et al. | |
| 2018/0296757 A1 | 10/2018 | Finan et al. | |
| 2018/0342317 A1 | 11/2018 | Skirble et al. | |
| 2018/0369479 A1 | 12/2018 | Hayter et al. | |
| 2019/0076600 A1 | 3/2019 | Grosman et al. | |
| 2019/0240403 A1 | 8/2019 | Palerm et al. | |
| 2019/0290844 A1 | 9/2019 | Monirabbasi et al. | |

(56) References Cited

U.S. PATENT DOCUMENTS

| | | | |
|---|---|---|---|
| 2019/0336683 A1 | 11/2019 | O'Connor et al. | |
| 2019/0336684 A1 | 11/2019 | O'Connor et al. | |
| 2019/0348157 A1 | 11/2019 | Booth et al. | |
| 2020/0046268 A1 | 2/2020 | Patek et al. | |
| 2020/0101222 A1 | 4/2020 | Lintereur et al. | |
| 2020/0101223 A1 | 4/2020 | Lintereur et al. | |
| 2020/0101225 A1 | 4/2020 | O'Connor et al. | |
| 2020/0121257 A1* | 4/2020 | Chan | G16H 20/10 |
| 2020/0219625 A1 | 7/2020 | Kahlbaugh | |
| 2020/0342974 A1 | 10/2020 | Chen et al. | |
| 2021/0050085 A1 | 2/2021 | Hayter et al. | |
| 2021/0077719 A1* | 3/2021 | Cardinali | G16H 10/60 |
| 2021/0098105 A1 | 4/2021 | Lee et al. | |
| 2021/0193285 A1* | 6/2021 | Nimri | G16H 40/40 |
| 2021/0335477 A1* | 10/2021 | Booth | G16H 40/63 |
| 2022/0023536 A1 | 1/2022 | Graham et al. | |
| 2022/0257857 A1* | 8/2022 | Dassau | A61M 5/142 |

FOREIGN PATENT DOCUMENTS

| | | | |
|---|---|---|---|
| CN | 1297140 A | 5/2001 | |
| DE | 19756872 A1 | 7/1999 | |
| EP | 0341049 A2 | 11/1989 | |
| EP | 0496305 A2 | 7/1992 | |
| EP | 0549341 A1 | 6/1993 | |
| EP | 1491144 A1 | 12/2004 | |
| EP | 1571582 A2 | 9/2005 | |
| EP | 0801578 B1 | 7/2006 | |
| EP | 2666520 A1 | 10/2009 | |
| EP | 2139382 A1 | 1/2010 | |
| EP | 2397181 A1 | 12/2011 | |
| EP | 2695573 A2 | 2/2014 | |
| EP | 2830499 A1 | 2/2015 | |
| EP | 2943149 A1 | 11/2015 | |
| EP | 3177344 A1 | 6/2017 | |
| EP | 3314548 A1 | 5/2018 | |
| EP | 2897071 B1 | 5/2019 | |
| EP | 3607985 A1 | 2/2020 | |
| GB | 2443261 A | 4/2008 | |
| JP | 51125993 A | 11/1976 | |
| JP | 02131777 A | 5/1990 | |
| JP | 2004283378 A | 10/2007 | |
| JP | 2017525451 A | 9/2017 | |
| JP | 2018153569 A | 10/2018 | |
| JP | 2019525276 A | 9/2019 | |
| TW | 200740148 A | 10/2007 | |
| TW | M452390 U | 5/2013 | |
| WO | 9800193 A1 | 1/1998 | |
| WO | 9956803 A1 | 11/1999 | |
| WO | 0030705 A1 | 6/2000 | |
| WO | 0032258 A1 | 6/2000 | |
| WO | 0172354 A2 | 10/2001 | |
| WO | 2002015954 A1 | 2/2002 | |
| WO | 0243866 A2 | 6/2002 | |
| WO | 02082990 A1 | 10/2002 | |
| WO | 03016882 A1 | 2/2003 | |
| WO | 03039362 A1 | 5/2003 | |
| WO | 03045233 A1 | 6/2003 | |
| WO | 2004043250 A1 | 5/2004 | |
| WO | 04092715 A1 | 10/2004 | |
| WO | 2005051170 A2 | 6/2005 | |
| WO | 2005082436 A1 | 9/2005 | |
| WO | 05110601 A1 | 11/2005 | |
| WO | 2005113036 A1 | 12/2005 | |
| WO | 2006053007 A2 | 5/2006 | |
| WO | 2007064835 A2 | 6/2007 | |
| WO | 2007078937 A1 | 7/2007 | |
| WO | 2008024810 A2 | 2/2008 | |
| WO | 2008029403 A1 | 3/2008 | |
| WO | 2008133702 A1 | 11/2008 | |
| WO | 2009045462 A1 | 4/2009 | |
| WO | 2009049252 A1 | 4/2009 | |
| WO | 2009066287 A3 | 5/2009 | |
| WO | 2009066288 A1 | 5/2009 | |
| WO | 2009098648 A2 | 8/2009 | |
| WO | 2009134380 A2 | 11/2009 | |
| WO | 2010053702 A1 | 5/2010 | |
| WO | 2010132077 A1 | 11/2010 | |
| WO | 2010138848 A1 | 12/2010 | |
| WO | 2010147659 A2 | 12/2010 | |
| WO | 2011095483 A1 | 8/2011 | |
| WO | 2012045667 A2 | 4/2012 | |
| WO | 2012108959 A1 | 8/2012 | |
| WO | 2012134588 A1 | 10/2012 | |
| WO | 2012177353 A1 | 12/2012 | |
| WO | 2012178134 A2 | 12/2012 | |
| WO | 2013078200 A1 | 5/2013 | |
| WO | 2013134486 A2 | 9/2013 | |
| WO | 20130149186 A1 | 10/2013 | |
| WO | 2013177565 A1 | 11/2013 | |
| WO | 2013182321 A1 | 12/2013 | |
| WO | 2014109898 A1 | 7/2014 | |
| WO | 2014110538 A1 | 7/2014 | |
| WO | 2014194183 A2 | 12/2014 | |
| WO | 2015056259 A1 | 4/2015 | |
| WO | 2015061493 A1 | 4/2015 | |
| WO | 2015073211 A1 | 5/2015 | |
| WO | 2015081337 A2 | 6/2015 | |
| WO | 2015187366 A1 | 12/2015 | |
| WO | 2016004088 A1 | 1/2016 | |
| WO | 2016022650 A1 | 2/2016 | |
| WO | 2016041873 A1 | 3/2016 | |
| WO | 2016089702 A1 | 6/2016 | |
| WO | 2016141082 A1 | 9/2016 | |
| WO | 2016161254 A1 | 10/2016 | |
| WO | 2017004278 A1 | 1/2017 | |
| WO | 2017091624 A1 | 6/2017 | |
| WO | 2017105600 A1 | 6/2017 | |
| WO | 2017184988 A1 | 10/2017 | |
| WO | 2017205816 A1 | 11/2017 | |
| WO | 2018009614 A1 | 1/2018 | |
| WO | 2018067748 A1 | 4/2018 | |
| WO | 2018120104 A1 | 7/2018 | |
| WO | 2018136799 A1 | 7/2018 | |
| WO | 2018204568 A1 | 11/2018 | |
| WO | 2019077482 A1 | 4/2019 | |
| WO | 2019094440 A1 | 5/2019 | |
| WO | WO-2019125932 A1 * | 6/2019 | A61M 5/1723 |
| WO | 2019213493 A1 | 11/2019 | |
| WO | 2019246381 A1 | 12/2019 | |
| WO | 2020081393 A1 | 4/2020 | |
| WO | 2021011738 A1 | 1/2021 | |
| WO | WO-2021005552 A1 * | 1/2021 | A61B 5/14532 |

OTHER PUBLICATIONS

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/w/index.php?title=Fuzzy_control_system&oldid=935091190.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Search Report for the European Patent Application No. 21168591.2, mailed Oct. 13, 2021, 04 pages.

International Search Report and Written Opinion for the International Patent Application No. PCT/US2021/041954, mailed Oct. 25, 2021, 13 pages.

International Search Report and Written Opinion for the International Patent Application No. PCT/US2021/047771, mailed Dec. 22, 2021, 11 pages.

International Search Report and Written Opinion for the International Patent Application No. PCT/US2021/052855, mailed Dec. 22, 2021, 11 pages.

(56) References Cited

OTHER PUBLICATIONS

International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-hfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.

International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, mailed Apr. 22, 2022, 15 pages.

(56)             References Cited

OTHER PUBLICATIONS

International Preliminary Report on Patentability in PCT/US2021/051027 issued on Mar. 21, 2023, 10 pages.

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

European Patent Office, "Notification of Transmittal of the ISR and the Written Opinion of the International Searching Authority, or the Declaration," in PCT Application No. PCT/GB2015/050248, Jun. 23, 2015, 12 pages.

Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

International Search Report and Written Opinion for the International Patent Application No. PCT/US2021/016283, mailed Jun. 2, 2021, 15 pages.

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Templeton et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood, " Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech, vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

International Search Report and Written Opinion for the International Patent Application No. PCT/US2021/022694, mailed Jun. 25, 2021, 13 pages.

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, mailed May 25, 2021, 12 pages.

International Search Report and Written Opinion for the InternationalPatent Application No. PCT/US2021/017664, mailed May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

(56) References Cited

OTHER PUBLICATIONS

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

* cited by examiner

_300_

_400_

Basal Delivery Parameter

Determine MDI
_402_

Determine TDI Based On MDI
_404_

Determine Basal Parameter Based On TDI
_406_

_500_

Maximum Additional Insulin

Determine Current And Target A1C
Difference
_502_

Determine Mean Blood Glucose
Difference Based On A1C Difference
_504_

Determine Total Additional Insulin
_506_

Set Total Additional Insulin As Maximum
Additional Automated Insulin Delivery
_508_

Deliver Basal Dosage
_514_

Yes

Maximum
Insulin
Delivered?
_510_

No

Deliver AID Dosage
_512_

TECHNIQUES FOR DETERMINING AUTOMATED INSULIN DELIVERY DOSAGES

FIELD OF THE INVENTION

The present disclosure generally relates to automated insulin delivery processes, and, more particularly, to processes for automated insulin delivery to treat diabetes.

BACKGROUND

Diabetes mellitus is a serious medical condition caused by an inability to adequately control blood glucose levels. Typical treatments involve injecting affected individuals with the hormone insulin in an attempt to maintain blood glucose values within a desired, healthy range. Type 1 diabetes mellitus (T1D) results from an autoimmune response in which the immune system attacks pancreatic beta cells so that they no longer produce insulin. For type 2 diabetes mellitus (T2D), the pancreas may produce insulin, but it is either not a sufficient amount and/or the body's cells do not adequately respond to the insulin.

Treatment advances for T1D patients have provided for automatic insulin delivery (AID) systems to control patient insulin levels. For example, an AID system may include a wearable insulin pump that operates to automatically inject insulin into the patient periodically or based on an event (for instance, user input, a determination that the patient blood sugar is below a threshold value, and/or the like). The dosage of insulin injected via the AID system may be determined based on historical information, blood glucose information measured using AID system sensors, and/or other factors (for instance, weight, ketones, manual information (for example, the patient is having a meal or the patient is exercising)), and/or the like.

Patients with advanced T2D also require regular insulin infusion. However, conventional treatments for T2D patients generally involve manual blood glucose measurements (for instance, finger-stick measurements) and needle injections performed by the patient. Conventional AID systems, which have been designed to treat T1D patients, are not able to directly operate for T2D patients because glucose metabolism and insulin kinetics are significantly different for T2D patients compared with T1D patients. Accordingly, it would be beneficial and advantageous to have a system, a device and/or a technique for safely and effectively providing automated delivery methods for providing insulin to T2D patients.

DETAILED DESCRIPTION

Figure 1:
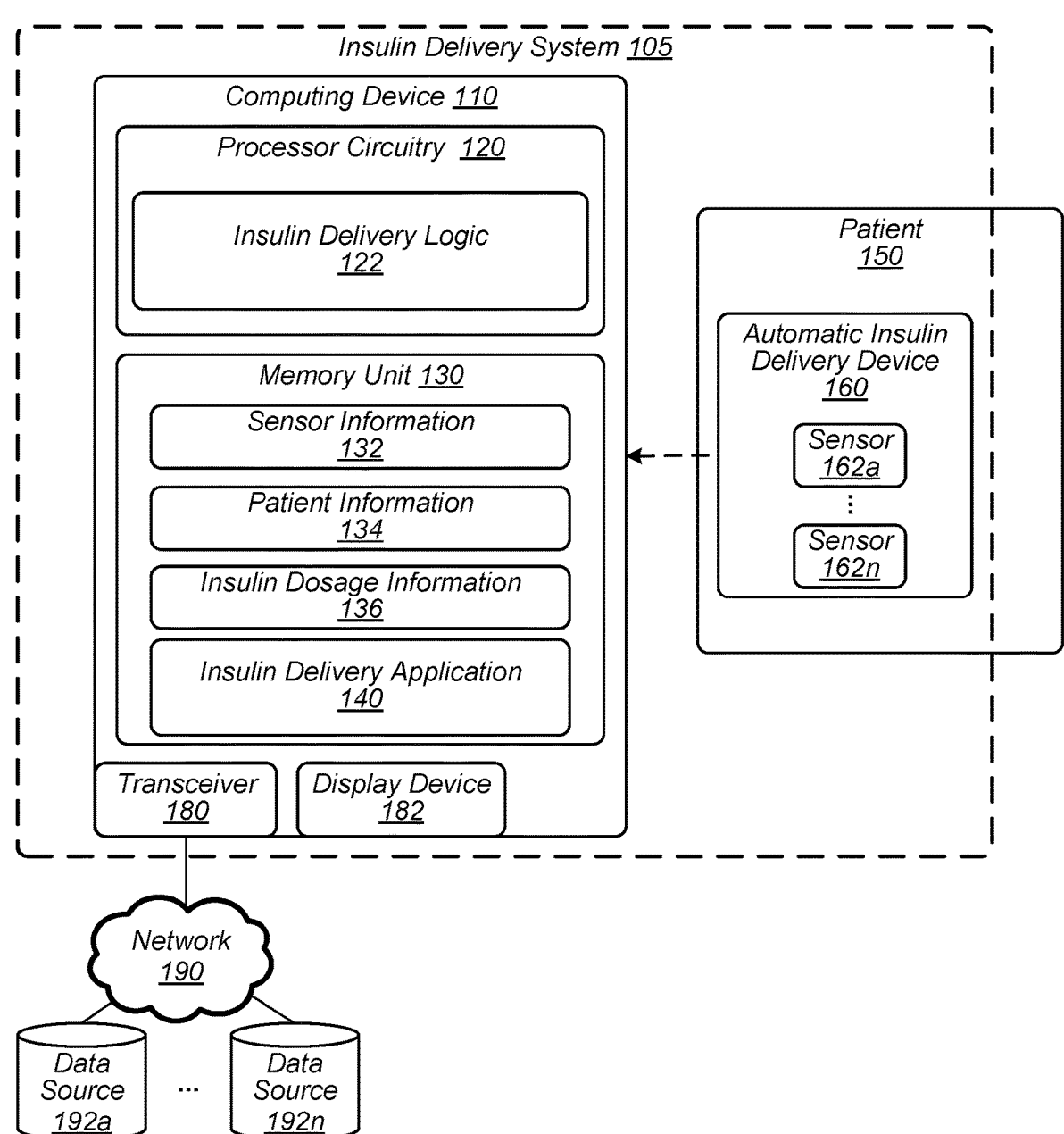
FIG. 1 illustrates a first exemplary operating environment in accordance with the present disclosure.

The described technology generally relates to an insulin infusion process for automatically infusing a patient with insulin. In some embodiments, an insulin infusion process may be used with additional processes, algorithms, or computer applications that manage blood glucose levels and/or other forms of insulin therapy. Such processes or algorithms may generally be referred to as an "artificial pancreas" (AP) system or application or an automatic insulin delivery (AID) system or application that may operate to provide automatic delivery of insulin. In some embodiments, the automatic delivery of insulin may be based, at least in part, on blood glucose information. In some embodiments, the blood glucose information may be obtained via sensor input, such as data measured via a continuous glucose monitor (CGM) device or sensor and/or from manual measurement (for instance, via a finger-stick measurement manually entered by a user).

Conventional AID systems have generally been developed to deliver insulin based on the needs of patients with Type 1 diabetes (T1D). However, patients with advanced Type 2 diabetes (T2D) also require regular insulin infusion and, accordingly, would benefit from an AID system that is tailored specifically to the needs of T2D patients that is efficient, accurate, and does not require complex intervention, such as manual estimations of blood glucose levels and/or insulin needs. There is significant difficulty in designing an optimal AID system for T2D patients using existing technology because, among other reasons, glucose metabolism, insulin kinetics, and other disease characteristics of T2D patients are significantly different than those for T1D patients. Therefore, AID systems developed to manage T1D cannot be directly transferred to treating T2D patients.

Accordingly, some embodiments may provide processes, devices, techniques, methods, and/or other technology for operating an AID system for implementing insulin therapy to treat T2D patients. For example, some embodiments may provide an insulin delivery process configured to utilize multiple daily injection (MDI) recommendations for T2D patients operative to provide a safe, accurate, and effective AID system that can reduce the burden of insulin delivery for T2D patients. Although T2D treatments and T2D patients may be used in examples in the present disclosure, embodiments are not so limited, as the insulin delivery processes of the present disclosure may be used for T1D and/or other conditions according to some embodiments.

A T2D patient typically receives basal insulin delivery via MDI (however, without compensation from bolus insulin for excursions, such as meals or food ingestions). Accordingly, some embodiments may provide an insulin delivery process operative to convert MDI therapy information for T2D patients into continuous subcutaneous insulin infusion (CSII) information, such as CSII rates for use with an AID system. In various embodiments, an insulin delivery process may be operative to set maximum additional insulin delivery based, for example, on differences between mean blood glucose and target blood glucose information. In exemplary embodiments, an insulin delivery process may be operative to determine and adjust safety constraints for providing insulin to T2D patients via an AID system. For example, insulin delivery processes may be configured to determine, adjust, or tune safety constraints to avoid hypoglycemia specifically for T2D patients, for example, accounting for the different characteristics and lower risks of hypoglycemia for T2D patients compared with T1D patients. In various embodiments, an insulin delivery process may be operative to deliver insulin using an AID system based on finger-stick blood glucose measurements (for example, instead of or in addition to CGM measurements).

Therefore, insulin infusion processes according to some embodiments may provide multiple technological advantages and technical features over conventional systems, including improvements to computing technology. One non-limiting example of a technological advantage may include determining AID processes based, at least in part, on conventional, manual T2D treatment information (for instance, MDI and/or total daily insulin (TDI) information). In this manner, T2D patients may be able to utilize automated processes and devices for treating T2D, experiencing the same or similar advantages for treatment, user experience, convenience, accuracy, efficiency, and/or the like available for AID treatment regimens. In another non-limiting example of a technological advantage, the computing technology of an AID device (including, for example, the wearable infusion device and/or a controller computing device) may be improved by being able to be controlled to implement an insulin infusion process according to some embodiments for treating T2D using the same or similar hardware (for example, conventionally used for T1D treatments). In a further non-limiting technological advantage, an AID system may operate to infuse a T2D patient with insulin using safety protocols and constraints specific for T2D patients without negatively affecting performance.

In addition, some embodiments may provide one or more practical applications of insulin infusion processes, algorithms, and/or the like described in the present disclosure. Illustrative and non-limiting practical applications may include treating diabetes, such as T2D, infusing a safe amount of insulin into a diabetic patient, operating an infusion device (for instance, an AID device) according to an insulin infusion process to provide a prescribed or predetermined amount of insulin that is safe and effective for a diabetic patient, converting conventional manual T2D information (for instance, MDI) into information configured to be used with an automated system, such as an AID system, and/or the like. Other technological advantages, improvements, and/or practical applications are provided by embodiments described in the present disclosure and would be understood by persons of skill in the art. Embodiments are not limited in this context.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In this Detailed Description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an insulin infusion system 105. In various embodiments, insulin infusion system 105 may include a computing device 110 that, in some embodiments, may be communicatively coupled to network 190 via a transceiver 180. Computing device 110 may be or may include a display device 182 and one or more logic devices, including, without limitation, a server computer, a client computing device, a personal computer (PC), a workstation, a laptop, a notebook computer, a smart phone, a tablet computing device, a personal diabetes management (PDM) device, and/or the like. Embodiments are not limited in this context.

Insulin infusion system 105 may include or may be communicatively coupled to an automatic insulin delivery (AID) device 160 configured to deliver insulin (and/or other medication) to patient 150. AID device 160 may be a wearable device. For example, AID device 160 may be directly coupled to patient 150 (for instance, directly attached to a body part and/or skin of the user via an adhesive and/or other attachment component).

AID device 160 may include a number of components to facilitate automated delivery of insulin to patient 150. For example, AID device 160 may include a reservoir for storing insulin, a needle or cannula for delivering insulin into the body of the person, and a pump for transferring insulin from the reservoir, through the needle or cannula, and into the body of the patient. AID device 160 may also include a power source, such as a battery, for supplying power to the pump and/or other components of automatic insulin delivery device 160. Embodiments are not limited in this context, for example, as AID device 160 may include more or less components.

AID device 160 may store and provide any medication or drug to the user. In various embodiments, AID device 160 may be or may include a wearable AID device. For example, AID device 160 may be the same or similar to an OmniPod® device or system provided by Insulet Corporation of Acton, Massachusetts, United States, for example, as described in U.S. Pat. Nos. 7,303,549; 7,137,964; and/or 6,740,059, each of which is incorporated herein by reference in its entirety.

In some embodiments, computing device 110 may be a smart phone, PDM, or other mobile computing form factor in wired or wireless communication with automatic insulin delivery device 160. For example, computing device 110 and AID device 160 may communicate via various wireless protocols, including, without limitation, Wi-Fi (i.e., IEEE 802.11), radio frequency (RF), Bluetooth™, Zigbee™, near field communication (NFC), Medical Implantable Communications Service (MICS), and/or the like. In another example, computing device 110 and adjustment compliance device may communicate via various wired protocols, including, without limitation, universal serial bus (USB), Lightning, serial, and/or the like. Although computing device 110 (and components thereof) and AID device 160 are depicted as separate devices, embodiments are not so limited. For example, in some embodiments, computing device 110 and AID device 160 may be a single device. In another example, some or all of the components of computing device 110 may be included in automatic insulin delivery device 160. For example, AID device 160 may include processor circuitry 120, memory unit 130, and/or the like. In some embodiments, each of computing device 110 and AID device 160 may include a separate processor circuitry 120, memory unit 130, and/or the like capable of facilitating insulin infusion processes according to some embodiments, either individually or in operative combination. Embodiments are not limited in this context (see, for example, FIG. 2).

AID device 160 may include or may be communicatively coupled to one or more sensors 162*a-n* operative to detect, measure, or otherwise determine various physiological characteristics of patient 150. For example, a sensor 162*a-n* may be or may include a CGM sensor operative to determine blood glucose measurement values of patient 150. In another example, a sensor 162*a-n* may include a heart rate sensor, temperature sensor, and/or the like.

Computing device 110 (and/or automatic insulin delivery device 160) may include a processor circuitry 120 that may include and/or may access various logics for performing processes according to some embodiments. For instance, processor circuitry 120 may include and/or may access an insulin delivery logic 122. Processing circuitry 120, insulin delivery logic 122, and/or portions thereof may be implemented in hardware, software, or a combination thereof. The functions, processes, algorithms, and/or the like (for example, an insulin infusion process) described according to some embodiments may be performed by processor circuitry and/or insulin delivery logic 122 (for example, via executing insulin delivery application 140) by computing device 110, automatic insulin delivery device 160, and/or a combination thereof. The processing circuitry 120, memory unit 130, and associated components are depicted within computing device 110 to simplify FIG. 1 (for instance, all or a portion of processing circuitry 120, memory unit 130, and associated components may be arranged within automatic insulin delivery device 160). Accordingly, embodiments of functionality, processes (for instance, an insulin infusion process), and/or the like described in the present disclosure with respect to computing device 110 and/or components thereof may be performed in whole or in part by automatic insulin delivery device 160.

As used in this application, the terms "logic," "component," "layer," "system," "circuitry," "decoder," "encoder," "control loop," and/or "module" are intended to refer to a computer-related entity, either hardware, a combination of hardware and software, software, or software in execution. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, FG circuitry, variations thereof, combinations of any of the foregoing, and/or the like.

Although insulin delivery logic 122 is depicted in FIG. 1 as being within processor circuitry 120, embodiments are not so limited. For example, insulin delivery logic 122 and/or any component thereof may be located within an accelerator, a processor core, an interface, an individual processor die, implemented entirely as a software application (for instance, an insulin delivery application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store various types of information and/or applications for an insulin infusion process according to some embodiments. For example, memory unit 130 may store sensor information 132, patient information 134, insulin dosage information 136, and/or insulin delivery application 140. In some embodiments, sensor information 132, patient information 134, insulin dosage information 136, insulin delivery application 140, and/or portions thereof may be stored in one or more data stores 192*a-n* accessible to computing device 110 (and/or automatic insulin delivery device 160) via network 190.

In some embodiments, insulin delivery application 140 may be or may include an application being executed on computing device 110 and/or AID device 160 (including a mobile application, "mobile app," or "app" executing on a mobile device form factor). For example, in various embodiments, insulin delivery application 140 may be or may include an application the same or similar to the Omnipod® Mobile App, Glooko, Omnipod® DASH™ PDM software, and/or the like provided by Insulet Corporation of Acton, Massachusetts, United States. In addition or in the alternative, insulin delivery application 140 may be or may include an application operative to control components of automatic insulin delivery device (for instance, a pump, sensors 162*a-n*, and/or the like) to infuse patient 150 with insulin, such as an AID application. For example, insulin delivery application 140 may be or may include an AID application to monitor patient blood glucose values, determine an appropriate level of insulin based on the monitored glucose values (e.g., blood glucose concentrations and/or blood glucose measurement values) and other information, such as user-provided information, including, for example, carbohydrate intake, exercise times, meal times, and/or the like, and perform an insulin infusion process according to some embodiments to maintain a user's blood glucose value within an appropriate range.

In some embodiments, sensor information 132 may include information determined via sensors 162*a-n*. For example, sensor information 132 may include CGM information (for instance, blood glucose concentrations or other blood glucose measurement values), temperature information, heart rate information, and/or the like. In exemplary embodiments, sensor information 132 may include historical information, for instance, historical blood glucose values of patient 150. In various embodiments, patient information 134 may include information associated with patient 150. Non-limiting examples of patient information 134 may include demographic information, physical information (for instance, height, weight, and/or the like), diabetes condition information (for instance, type of diagnosed diabetes (T1D or T2D)), insulin needs (for instance, MDI information, TDI information, insulin types, and/or the like), activity information (for instance, meals and/or meal times, carbohydrate intake, exercise information, and/or the like), insulin sensitivity information, and/or the like. In some embodiments, at least a portion of patient information 134 may be manually entered by patient 150 or a caregiver, for example, via a user interface of insulin delivery application 140. In some embodiments, patient information 134 may include historical information, such as historical values associated with mealtimes, carbohydrate intake, exercise times, and/or the like.

In some embodiments, insulin dosage information 136 may include information used to perform an insulin infusion process via AID device 160 according to some embodiments. Non-limiting examples of insulin infusion information may include MDI information, TDI information, CGM information, basal dosage information, basal rate information, basal parameter(s), current glycated hemoglobin (HbA1c or "A1C") information, target A1C information, blood glucose difference (for instance, $BG_{diff}$), correction factor parameter(s) (CF), maximum additional insulin delivery information ($I_{add}$), AID process or algorithm information, safety constraint information, adjustment factor(s) ($F_s$), thresholds (for example, total insulin delivery during a certain duration, insulin-on-board (IOB), IOB decay rate (D(t)), and/or the like), change in basal (for example, Ab(i)), insulin sensitivity factors, constants, tunable parameters, and/or the like.

Insulin delivery logic 122, for example, implemented via insulin delivery application 140 being executed by processor circuitry 120, may operate to perform an insulin infusion process according to some embodiments to infuse a patient with insulin. In various embodiments, the insulin infusion process may be configured for a T2D patient.

In some embodiments, the insulin infusion process may operate to determine insulin dosage information 136 in the form of a basal parameter for patient 150. The basal parameter may be used by the insulin infusion process, for example, via an associated AID algorithm, to deliver a dosage of insulin to patient 150. For example, the basal parameter may be or may be used for determining continuous insulin infusion (CII) rate. A non-limiting example of a CII may be or may include continuous subcutaneous insulin infusion (CSII) information. However, embodiments are not limited to subcutaneous infusion (for instance, insulin delivery may occur at the dermal layer of the skin of patient 150). In some embodiments, the basal parameter may be the basal insulin needs of patient 150.

In some embodiments, insulin delivery logic 122 may implement the insulin infusion process to convert MDI insulin quantities of patient 150 into CII (or CSII) for use in an AID algorithm. For example, T2D patients may utilize one or more daily injections (MDI) of insulin per day of a fixed quantity of (long-acting) insulin for each injection. For instance, patient 150 may be a T2D patient having an MDI protocol requiring two injections of 20 units (U) of long-acting insulin, for a TDI total of 40 U per day. In various embodiments, the total amount of insulin (TDI or total daily dosage (TDD)) to be delivered may be converted into a basal parameter. For example, in some embodiments, it may be assumed that T2D patients often do not bolus for their meals such that the entirety of the insulin deliveries each day can be considered to be their basal needs, instead of the typical assumption of utilizing 50% of the total insulin deliveries as their basal needs (for instance, for T1D patients used in conventional AID algorithms).

The following Equation (1) may be used to determine TDI based on MDI:

$$TDI = \sum_{n=1}^{n_{max}} MDI_n,$$

where $MDI_n$ is the $n^{th}$ injection of patient 150. The following Equation (2) may be used to determine the basal parameter based on TDI:

$$basal = \frac{TDI}{24}.$$

In various embodiments, the basal parameter may be used as input to an AID algorithm, for example, to determine an infusion rate, total infusion dosage, and/or the like. In Equation (2), the value 24 may indicate a 24-hour period for the basal parameter. Other values may be substituted for other time periods (for instance, 48 for ½ hour time periods, 144 for 10-minute time periods, 288 for 5-minute time periods, and so on). For example, for a patient having a TDI of 45 units, the basal parameter may be about 1.875 units/hour for an AID algorithm infusion rate.

In some embodiments, the insulin infusion process may determine a maximum daily dosage of insulin. In various embodiments, the maximum daily dosage may be determined based, at least in part, on target health conditions for patient 150. For example, in one embodiment, the maximum daily dosage may be determined based on a target A1C for patient 150. A1C is an important factor in assessing the quality of blood glucose control for people with T2D. In general, A1C is a percentage indicating patient blood sugar levels over a previous time period, typically two to three months. A normal A1C (for instance, of a non-diabetic individual) may be a value less than about 6.0%. A target A1C for T2D patients may be about 7.0%; however, each patient may have their own target A1C. Diabetes management of people with T2D often have a target A1C, for example, that is lower than their current A1C.

In some embodiments, the difference between the current A1C and the target A1C may be converted into a difference in mean blood glucose ($BG_{diff}$) according to the following Equation (3):

$$A1C_{current} - A1C_{target} = \frac{BG_{diff} + 68.8}{31.5}.$$

In various embodiments, the basal needs of patient 150 (for instance, the basal parameter) may be used to estimate a correction factor (CF) parameter (for instance, for T2D patients). In some embodiments, CF may be determined by converting the basal parameter to daily needs using an insulin sensitivity factor. In some embodiments, the insulin sensitivity factor may be the "1800 rule" or other similar sensitivity factor for indicating patient reactions to insulin (for instance, the 1800 rule may be used to determine how much a patient's blood sugar may drop for each unit of a particular type of insulin by dividing 1800 by the number of units of insulin delivered over an infusion time period). In various embodiments, each patient may have their own sensitivity factor. For example, in an embodiment, CF may be determined for the 1800 rule according to the following Equation (4):

$$CF = \frac{1800}{24 * \text{basal}},$$

where 24 indicates 24 hours per day (an infusion time period) and the 1800 (infusion sensitivity factor) may be substituted based on the particular insulin sensitivity used to determine CF.

In exemplary embodiments, the insulin infusion process may use the difference in mean BG (for instance, $BG_{diff}$) to determine an expected total additional insulin need per day ($I_{add}$) according to the following Equation (5):

$$I_{add} = \frac{BG_{diff}}{CF} * 6,$$

where the value 6 is a tunable cycle parameter configured to represent the number of 4-hour cycles of insulin peak times per 24-hour period. Accordingly, Equation (5) may use different cycle parameter values other than 6 depending on, for instance, the specific treatment regimen and/or physiological characteristics of patient 150. In some embodiments, $I_{add}$ may be insulin to be delivered to a patient in addition to the volume indicated by the basal parameter (for instance, bolus insulin requirements) to achieve diabetic therapy goals for patient 150.

In various embodiments, $I_{add}$ may be set as the maximum additional delivery of insulin allowed for patient 150 (for instance, the maximum allowed beyond TDI or basal). In some embodiments, $I_{add}$ may be set as the maximum additional delivery of insulin allowed for patient 150 within a basal parameter time period (for instance, 24-hour time period) by AID device 160. For example, in various embodiments, the actual insulin delivery by AID device 160 may be defined according to the following Equation (6):

$$I_{AID}(t) = \begin{cases} AID_{alg}(t) & \sum_{i=1}^{T} AID_{alg}(i) - \text{basal}(i) \le \text{basal} * T \\ b(t) & \sum_{i=1}^{T} AID_{alg}(i) - \text{basal}(i) > \text{basal} * T \end{cases},$$

where t is the current control cycle where the actual insulin delivery decision may be made, T is the time unit of consideration to apply this limit (for instance, 1 for hour 1, 2 for hour 2, and so on), $I_{AID}(t)$ is the amount of insulin to be infused into patient 150 at time t, $AID_{alg}(t)$ is the amount of insulin determined for infusion according to the AID algorithm associated with AID device 160 at time t, and basal(t) is the basal units to be delivered at time t (for example, if basal is 30 units per day and t is 24 (for instance, infusion every hour), then basal(t) is 30/24=1.25). With reference to Equation (6), delivery of insulin according $AID_{alg}(t)$ may occur if the maximum delivery limit has not been reached, and basal (b(t)) may be delivered if the maximum delivery limit has been reached. For example, $I_{AID}$ may be or may be considered $AID_{alg}$ if the sum of differences between $AID_{alg}$-basal is less than the threshold, and basal if $AID_{alg}$-basal is greater than the threshold. In some embodiments, the maximum delivery limit may be determined based on (basal parameter)+$I_{add}$. Accordingly, in some embodiments, the insulin infusion process may use Equation (6) to limit the automated insulin delivery to basal in a binary manner by comparing against the additional insulin delivery ($I_{add}$).

In one exemplary embodiment, the threshold for maximum insulin delivery allowed beyond the user's basal per 24 hour period can be set to 6 hours (T=6). In this example, defining T=6 may mean that the system cannot deliver more than 6 times basal, above the user's basal, in total, over the last 6 hours. Thus, at any cycle t, the system may take the sum of insulin deliveries in the last 6 hours, corresponding to the first term in the summation portion of Equation 6. In this example, for instance, the total delivery may be 15 U of insulin and basal may be 2 U/hour. Then, the sum of the total insulin delivery minus the total basal in the last 6 hours is 3 U. This is less than 12U, which is the stated maximum insulin delivery allowed above basal in this example. As a result, the system would deliver the full insulin delivery request as defined by $AID_{alg}(t)$ for the current cycle t. On the other hand, if the total delivery was 25 U, the user received 13 U above basal, which exceeds the stated threshold of 12 U. In this case, the system would deliver the basal value b(t) instead of $AID_{alg}(t)$ in the current cycle t.

In various embodiments, the insulin infusion process may include determining one or more safety constraints or safety constraint adjustments. In some embodiments, the safety constraint adjustments may be based, at least in part, on additional insulin delivery ($I_{add}$) requirements. In exemplary embodiments, the safety constraints may be adjusted to allow a continuous limitation of AID device 160 insulin delivery that still allows for delivery of an amount of insulin beyond $I_{add}$ as necessary.

Specifically, safety constraints within an AID algorithm may be associated with, at least in some form, to the patient TDI. For example, because $I_{add}$ may represent the additional total insulin delivery, the safety constraints may be adjusted (for example, relaxed) by an adjustment factor. For instance, the safety constraints may be relaxed by a percentage adjustment ($F_s$) based on the proportion of $I_{add}$ versus the user's TDI, according to the following Equation (7):

$$F_s = 1 + \max\left(0, \frac{I_{add}}{TDI}\right).$$

In some embodiments, the insulin infusion process may include a duration maximum threshold (or integral delivery) safety constraint. For example, the duration maximum factor may provide that the total insulin delivery for patient 150 during a certain duration (for example, 3 hours) cannot exceed a tunable factor (for instance, 9) times the basal parameter. The adjustment factor can affect (for example, increase) the duration maximum threshold, for instance, by multiplying the duration maximum threshold by $F_s$ as provided in the following Equation (8):

$$\text{Duration Maximum (or } th_{integral,mod}) = 9 * \frac{TDI}{48} * F_s,$$

where 9 is the tunable factor and the value 48 may be modified based on the duration of interest.

In various embodiments, the insulin infusion process may include an insulin-on-board (IOB) safety constraint. In some embodiments, the IOB safety constraint may include determining insulin delivery in deviations from basal as a baseline. The IOB baseline (for instance, $th_{IOB}$) may be affected (for example, increased) by the adjustment factor $F_s$ according to the following Equation (9):

$$th_{IOB} = \sum_{i=1}^{t} D(t) * (I(t) - \text{basal} * F_s),$$

where D(t) is an IOB decay rate tunable parameter.

In some embodiments, the insulin infusion process may operate AID device 160 insulin delivery based on manual blood glucose measurement instead of or in addition to CGM measurement processes. For example, the insulin infusion process may be configured to operate AID device 160 to automatically calculate adjustments in insulin delivery whenever patient 150 measures a fingerstick glucose value. In some embodiments, for instance, insulin delivery adjustments may be determined according to the following Equation (10):

$$\Delta b(i) = (BG(i) - \text{target}) * TDI * C,$$

where $\Delta b(i)$ represents the change in basal of patient 150 based on the $i^{th}$ fingerstick glucose (BG) measurement, and C is a tunable constant. In various embodiments, the manual fingerstick-based blood glucose meter (BG meter) may be communicatively coupled to AID device 160, for instance, via Bluetooth or another wired or wireless communication protocol. Accordingly, in various embodiments, the $\Delta b(i)$ adjustment may be automatically implemented if AID device 160 is connected to the BG meter.

In various embodiments, tunable constant C may be determined assuming, for example, the insulin sensitivity of patient 150 (for instance, using the 1800 rule), and estimating or otherwise determining that the insulin delivery may occur over a delivery duration (for instance, 8 hours or the maximum duration of insulin action of patient 150) according to the following Equation (11):

$$C = \frac{1}{1800 * 8},$$

where the value 1800 may be substituted for other insulin sensitivity rules and 8 may be substituted for other maximum durations of insulin action.

In some embodiments, the $\Delta b(i)$ adjustment may also be made asymmetric and/or dependent on the current blood glucose of patient 150. In various embodiments, for example, the $\Delta b(i)$ adjustment may be modified by the value of the current blood glucose measurement according to the following Equation (12):

$$\Delta b(i) = \begin{cases} (BG(i) - \text{target}) * TDI * C & BG(i) > 70 \\ 0 & BG(i) \le 70 \end{cases}.$$

In exemplary embodiments, the insulin infusion process may modify the assumed rate t which insulin may take action based on the current blood glucose measurement of patient 150, for example, by adjusting the maximum durations of insulin action value (for instance, the "8" value in Equation (11)) of the C constant according to the following Equation (13):

$$C = \begin{cases} \dfrac{1}{1800 * 8} & BG(i) > \text{target} \\ \dfrac{1}{1800 * 7} & 70 < BG(i) \le \text{target} \\ \dfrac{1}{1800 * 6} & BG(i) \le 70 \end{cases}.$$

Accordingly, in some embodiments, insulin delivery may be adjusted (for instance, decreased) more rapidly if the blood glucose of patient 150 is below the target.

In various embodiments, instead of using a flat or semi-flat adjustment to a safety constraint, the safety constraints may be individually modified, for example, to correspond or match the insulin dynamics of T1D patients. For example, the need for additional insulin, combined with less likelihood of T2D patients experiencing hypoglycemic risk, may allow for direct adjustment of the time constants of the constraints in addition to the TDI baselines. For instance, the "3 hour" constraint of the integral delivery constraint may instead by set to a "2 hour" constraint; similarly, the insulin decay curve D(t) can be set to decay X % (accelerated decay factor) faster corresponding to $F_s$. For example, the accelerated decay factor may be about 1%, about 5%, about 10%, about 20%, about 30%, about 40%, about 50%, about 60%, about 70%, about 80%, about 90%, about 95%, or any values or ranges between any two of these values (including endpoints). Embodiments are not limited in this context.

Figure 2:
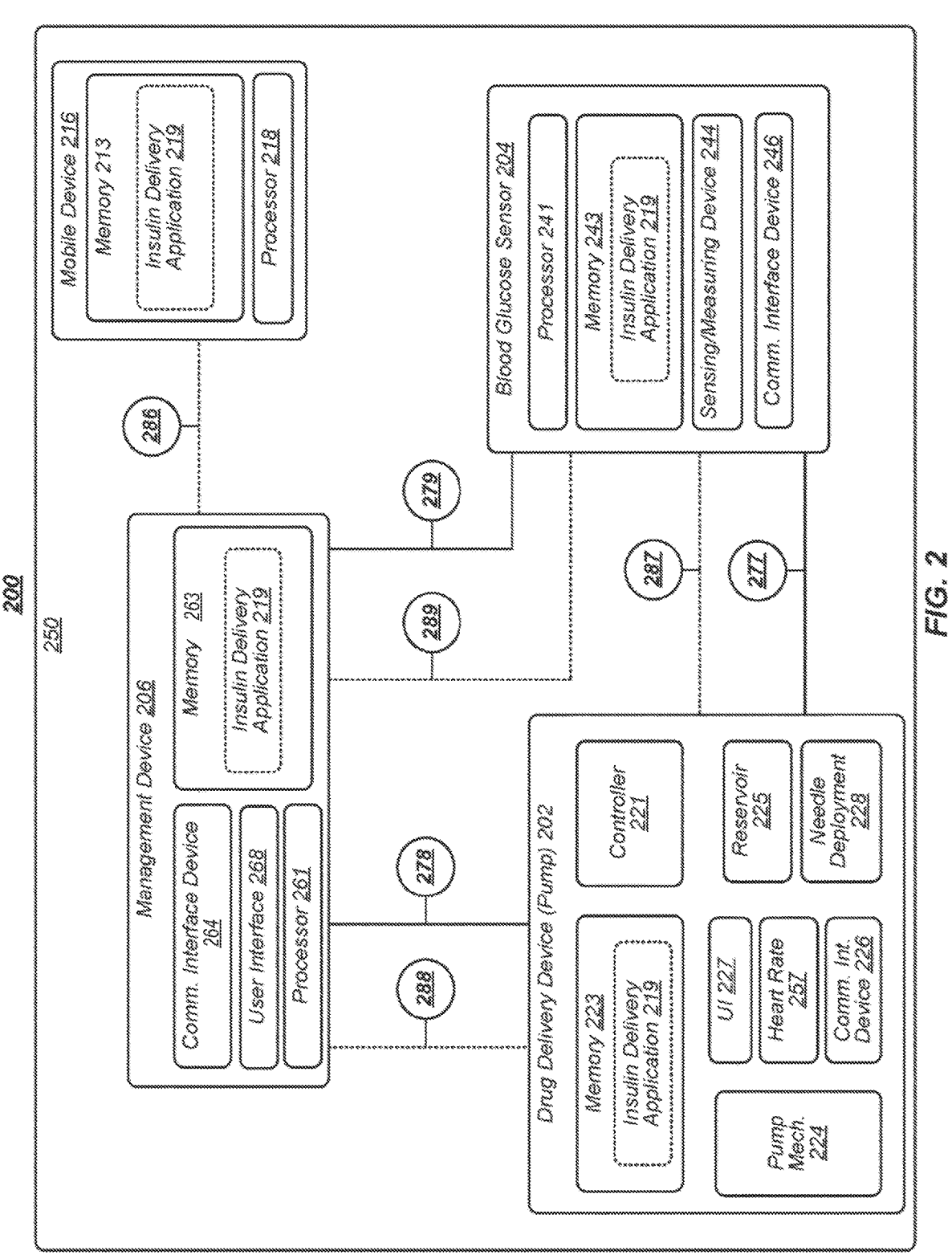
FIG. 2 illustrates a second exemplary operating environment in accordance with the present disclosure.

FIG. 2 illustrates a second exemplary operating environment in accordance with the present disclosure. More specifically, FIG. 2 illustrates an example of an operating environment 200 implementing a drug delivery system that utilizes one or more examples of the insulin infusion process according to some embodiments, for example, as described with reference to FIGS. 1 and 3-6. In some embodiments, drug delivery system 250 may be an implementation of operating environment 100 of FIG. 1 (or vice versa).

As shown in FIG. 2, drug delivery system 250 may include a drug delivery device 202, a management device 206, and a blood glucose sensor 204. In some embodiments, drug delivery device 202 may be a wearable or on-body drug delivery device that is worn on the body of a patient or user. Drug delivery device 202 may include a pump mechanism 224 that may, in some examples be referred to as a drug extraction mechanism or component, and a needle deployment component 228. In various examples, the pump mechanism 224 may include a pump or a plunger (not shown).

Needle deployment component 228 may, for example, include a needle (not shown), a cannula (not shown), and any other fluid path components for coupling the stored liquid drug in reservoir 225 to the user. The cannula may form a portion of the fluid path component coupling the user to reservoir 225. After needle deployment component 228 has been activated, a fluid path (not shown) to the user is provided, and pump mechanism 224 may expel the liquid drug (for instance, insulin) from reservoir 225 to deliver the liquid drug to the user via the fluid path. The fluid path may, for example, include tubing (not shown) coupling wearable drug delivery device 202 to the user (e.g., tubing coupling the cannula to reservoir 225).

Wearable drug delivery device 202 may further include a controller 221 (for instance, the same or similar to processing circuitry 120) and a communications interface device 226. Controller 221 may be implemented in hardware, software, or a combination thereof. The controller 221 may, for example, be a processor, a logic circuit or a microcontroller coupled to a memory 223. Controller 221 may maintain a date and time as well as other functions (e.g., calculations or the like) performed by processors. Controller 221 may be operable to execute an AP or AID application, for example, insulin delivery application 219 stored in memory 223 that enables controller 221 to direct operation of drug delivery device 202. In addition, controller 221 may be operable to receive data or information indicative of physiological characteristics of the user from mobile device 216, blood glucose sensor 204, management device 206, and/or the like.

In some embodiments, drug delivery device 202 may include or may be communicatively coupled to a blood glucose sensor 204. In some embodiments, blood glucose sensor 204 may be a CGM sensor. In various embodiments, blood glucose sensor 204 may be a fingerstick-based blood glucose sensor. Blood glucose sensor 204 may be physically separate from drug delivery device 202 or may be an integrated component thereof. In various embodiments, blood glucose sensor 204 may provide controller 221 with data indicative of measured or detected blood glucose (BG) levels of the user. In some embodiments, a user may manually enter blood glucose measurements, for instance, measured via a fingerstick method into management device 206, mobile device 216, drug delivery device 202, and/or management device 206 for use by drug delivery device 202.

Management device 206 (for instance, a PDM) may be maintained and operated by the user or a caregiver of the user. Management device 206 may control operation of drug delivery device 202 and/or may be used to review data or other information indicative of an operational status of drug delivery device 202 or a status of the user. Management device 206 may be used to direct operations of drug delivery device 202. For example, management device 206 may be a dedicated personal diabetes management (PDM) device, a smartphone, a tablet computing device, other consumer electronic device including, for example, a desktop, a laptop, a tablet, or the like. Management device 206 may include a processor 261 and memory devices 263. In some embodiments, memory devices 263 may store an insulin delivery application 219 that may be or may include an AP or AID application including programming code that may implement delivery of insulin based on input from blood glucose sensor 204 (for instance, via a CGM-based blood glucose sensor 204 and/or a fingerstick-based blood glucose sensor 204) and/or manual user input.

In some embodiments, management device 206 may operate in cooperation with a mobile device 216. In various embodiments, mobile device 216 may include a memory 213 and a processor 218 as well as additional components and elements as discussed with reference to computing device 110 of FIG. 1. Memory 213 may store programming code as well as mobile computer applications, such as insulin delivery application 219

In an example, wearable drug delivery device 202 may be attached to the body of a user, such as a patient or diabetic, and may deliver any therapeutic agent, including any drug or medicine, such as insulin or the like, to a user. Wearable drug delivery device 202 may, for example, be a wearable device worn by the user. For example, wearable drug delivery device 202 may be directly coupled to a user (e.g., directly attached to a body part and/or skin of the user via an adhesive or the like). In an example, a surface of the wearable drug delivery device 202 may include an adhesive to facilitate attachment to a user. Wearable drug delivery device 202 may be referred to as a pump, or an insulin pump, in reference to the operation of expelling a drug from reservoir 225 for delivery of the drug to the user.

In an example, wearable drug delivery device 202 may include a reservoir 225 for storing the drug (such as insulin), a needle or cannula (not shown) for delivering the drug into the body of the user (which may be done subcutaneously, intraperitoneally, or intravenously), and a pump mechanism 224, or other drive mechanism, for expelling the stored insulin from the reservoir 225, through a needle or cannula (not shown), and into the user. Reservoir 225 may be operable to store or hold a liquid or fluid, such as insulin or another therapeutic drug. Pump mechanism 224 may be fluidly coupled to reservoir 225, and communicatively coupled to controller 221. Wearable drug delivery device 202 may also include a power source (not shown), such as a battery, a piezoelectric device, or the like, for supplying electrical power to pump mechanism 224 and/or other components (such as controller 221, memory 223, and communication interface device 226) of wearable drug delivery device 202.

In an example, blood glucose sensor 204 may be a CGM device communicatively coupled to the processor 261 or controller 221 and may be operable to measure a blood glucose value at a predetermined time interval, such as approximately every 5 minutes, or the like. Blood glucose sensor 204 may provide a number of blood glucose measurement values to the insulin delivery application 219 operating on the respective devices. In another example, blood glucose sensor 204 may be a manual blood glucose sensor measuring blood glucose in blood from a fingerstick method.

Wearable drug delivery device 202 may operate to provide insulin stored in reservoir 225 to the user based on information (for instance, insulin dosage information 136) determined via an insulin infusion process according to some embodiments. For example, wearable drug delivery device 202 may contain analog and/or digital circuitry that may be implemented as a controller 221 (or processor) for controlling the delivery of the drug or therapeutic agent. The circuitry used to implement controller 221 (the same or similar to processing circuitry 120) may include discrete, specialized logic and/or components, an application-specific integrated circuit, a microcontroller or processor that executes software instructions, firmware, programming instructions or programming code (for example, insulin delivery application 140 as well as the process examples of FIGS. 3-6) stored in memory 223, or any combination thereof. For example, controller 221 may execute a control algorithm, such an AID algorithm of insulin delivery application 219, that may make the controller 221 operable to cause pump mechanism 224 to deliver doses of the drug or therapeutic agent to a user at predetermined intervals or as needed to bring blood glucose measurement values to a target blood glucose value based on the insulin infusion process according to some embodiments.

The devices in system 250, such as management device 206, wearable drug delivery device 202, and sensor 204, may also be operable to perform various functions including controlling wearable drug delivery device 202. For example, management device 206 may include a communication interface device 264, a processor 261, and a management device memory 263. In some embodiments, management device memory 263 may store an instance of insulin delivery application 219.

In some embodiments, sensor 204 of system 250 may be a continuous glucose monitor (CGM) or a manual glucose sensor, that may include a processor 241, a memory 243, a sensing or measuring device 244, and/or a communication interface device 246. Memory 243 may store an instance insulin delivery application 219 as well as other programming code and may be operable to store data related to insulin delivery application 219

Instructions for determining the delivery of the drug or therapeutic agent (e.g., as a bolus dosage) to the user (e.g., the size and/or timing of any doses of the drug or therapeutic agent) may originate locally by wearable drug delivery device 202 or may originate remotely and be provided to wearable drug delivery device 202. In an example of a local determination of drug or therapeutic agent delivery, programming instructions, such as an instance of the insulin delivery application 219, stored in the memory 223 that is coupled to wearable drug delivery device 202 may be used to make determinations by wearable drug delivery device 202. In addition, wearable drug delivery device 202 may be operable to communicate via communication interface device 226 and wireless communication link 288 with wearable drug delivery device 202 and with blood glucose sensor 204 via communication interface device 226 and wireless communication link 287.

In addition or alternatively, remote instructions may be provided to wearable drug delivery device 202 over a wired or wireless link by the management device (PDM) 206. For example, PDM 206 may be equipped with a processor 261 that may execute an instance of the insulin delivery application 219 resident in the memory 263. Wearable drug delivery device 202 may execute any received instructions (originating internally or from management device 206) for the delivery of insulin to the user. In this manner, the delivery of the insulin to a user may be automated.

Devices within insulin delivery system 250 may be configured to communicate via various wired links 277-279 and/or wireless links 286-289. Wired links 277-279 may be any type of wired link provided by any known or future wired communication standard. Wireless links 286-289 may be any type of wireless link provided by any known or future wireless standard. As an example, wireless links 286-289 may enable communications between wearable drug delivery device 202, management device 206, sensor 204 based, and/or mobile device 216 on, for example, Bluetooth®, Wi-Fi®, a near-field communication standard, a cellular standard, or any other wireless optical or radio-frequency protocol. In some embodiments, mobile device 216 may operate as a management device 206 (for instance, management device 206 may not be a separate PDM device; rather, PDM functions are performed via insulin delivery application 219 operating on mobile device 216).

Although sensor 204 is depicted as separate from wearable drug delivery device 202, in various examples, sensor 204 and wearable drug delivery device 202 may be incorporated into the same unit. For example, sensor 204 may be a part of wearable drug delivery device 202 and contained within the same housing of wearable drug delivery device 202. Blood glucose measurement information (whether automatically or manually (fingerstick) determined) determined by sensor 204 may be provided to wearable drug delivery device 202 and/or management device 206, which may use the measured blood glucose values to determine an infusion amount or rate based on an insulin infusion process according to some embodiments.

In some examples, wearable drug delivery device 202 and/or management device 206 may include a user interface 227 and 268, respectively, such as a keypad, a touchscreen display, levers, buttons, a microphone, a speaker, a display, or the like, that is operable to allow for user input and/or output to user (for instance, a display of information). The wearable drug delivery device 202 may further include a heart rate sensor 257

In some embodiments, drug delivery system 250 may implement an AP or AID algorithm (for instance, insulin delivery application 219) to govern or control automated delivery of insulin to a user based on an insulin infusion process according to some embodiments. Insulin delivery application 219 may be used to determine the times and dosages of insulin delivery (for example, a rate based on the basal parameter, $I_{add}$, adjustment factors, safety constraints, and/or the like). In various examples, the insulin delivery application 219 may determine the times and dosages for delivery based, at least in part, on information known about the user, such as gender, age, weight, height, and/or other information gathered about a physical attribute or condition of the user (e.g., from the sensor 204).

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 3:
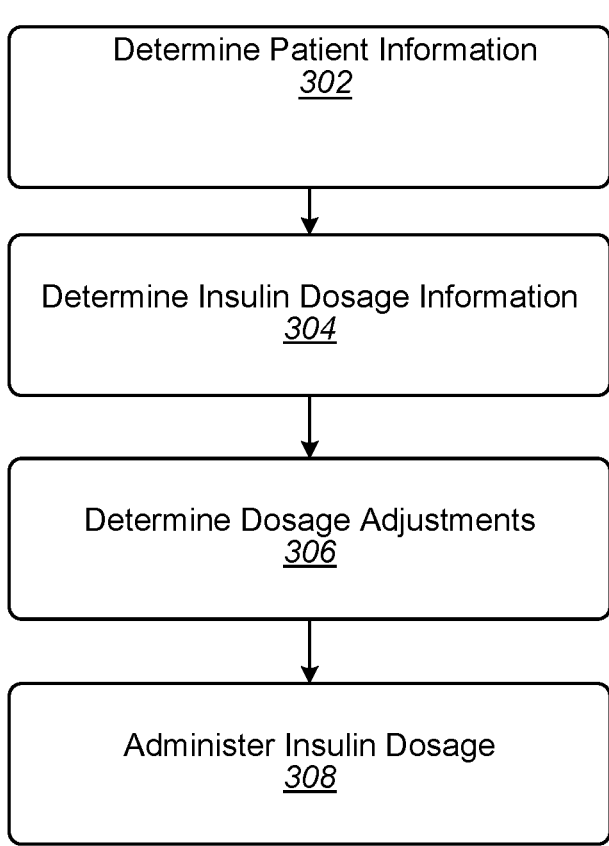
FIG. 3 illustrates a first logic flow in accordance with the present disclosure.

FIG. 3 illustrates an embodiment of a logic flow 300. Logic flow 300 may be representative of some or all of the operations executed by one or more embodiments described herein, such as devices of operating environments 100 and/or 200. In some embodiments, logic flow 300 may be representative of some or all of the operations of an insulin infusion process according to some embodiments.

At block 302, logic flow 300 may determine patient information. For example, patient 150 or caregiver for patient 150 may enter patient information 134 into computing device 110, for instance, via a user interface of insulin delivery application 140. In another example, insulin delivery application 140 may access patient information stored in data sources 192*a-n*, such as electronic medical records. In various embodiments, patient information 134 may include patient demographic information, physiological information, and/or insulin dosage information. For example, patient 150 may be a T2D patient using MDI-based therapy to manage their diabetic condition. In such an example, patient information 134 may include MDI information for patient 150.

Logic flow 300 may determine insulin dosage information at block 304. For example, insulin delivery application 140 may determine TDI for patient 150 based on MDI information, for instance, via Equation (1), and then determine a basal parameter for patient 150 based on the TDI, for instance, according to Equation (2) (see, for example, FIG. 4). In addition, insulin delivery application 140 may determine the maximum daily additional insulin ($I_{add}$) for patient, for example, based on current and target A1C levels for patient 150 via Equation (5) (see, for example, FIG. 5). In various embodiments, insulin delivery application 140 may use the basal parameter and $I_{add}$ to determine insulin dosage information 136, such as an infusion rate, an injection volume for an injection cycle, and/or the like.

At block 306, logic flow 300 may determine dosage adjustments. For example, insulin delivery application 140 may determine safety constraints for the insulin infusion process, such as an AID algorithm for determining that automated insulin dosage for an infusion cycle. Non-limiting examples of safety constraints may include a duration maximum safety constraint (see, for instance, Equation (8)) and/or an IOB safety constraint (see, for example, Equation (9)).

Logic flow 300 may administer the insulin dosage at block 308. For example, insulin delivery application 140 may instruct, manage, control, or otherwise cause AID device 160 to deliver a dosage of insulin to patient 150 determined based on the insulin infusion process according to some embodiments. The insulin dosage may include a volume of insulin (which may include no insulin or a volume of 0 units) determined based on the basal parameter, $I_{add}$, adjustment factors, safety constraints, and/or processes of an AID algorithm.

Figure 4:
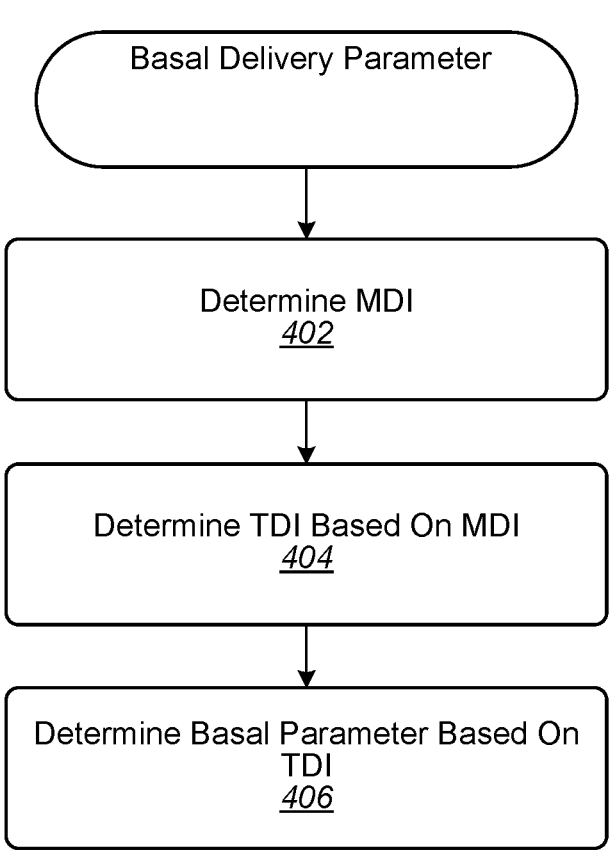
FIG. 4 illustrates a second logic flow in accordance with the present disclosure

FIG. 4 illustrates an embodiment of a logic flow 400. Logic flow 400 may be representative of some or all of the operations executed by one or more embodiments described herein, such as devices of operating environments 100 and/or 200. In some embodiments, logic flow 400 may be representative of some or all of the operations of an insulin infusion process for determining a basal parameter according to some embodiments.

At block 402, logic flow 400 may determine MDI. For example, insulin delivery application 140 may receive patient information indicating MDI for patient 150, for instance, according to a T2D treatment regimen for patient 150. The MDI information may be entered manually by patient 150 or a caregiver of patient 150 and/or may be determined by insulin delivery application 140 based on patient characteristics, physician instructions or recommendations, treatment protocols, and/or the like. For example, patient 150 may have an MDI treatment plan of two injections of 20 units of long-acting insulin and 1 injection of 10 units of long-acting insulin.

Logic flow 400 may determine TDI based on MDI at block 404. For example, insulin delivery application 140 may use Equation (1) to determine TDI based on MDI for patient 150. For example, for an MDI of two injections of 20 units of long-acting insulin and 1 injection of 10 units of long-acting insulin, Equation (1) may determine a TDI of 50 units of insulin. At block 406, logic flow 400 may determine a basal parameter based on TDI. For example, insulin delivery application 140 may use Equation (2) to determine a basal parameter based on the TDI determined at block 404. In an example, for a TDI of 50 units, the basal parameter may be 50/24=2.08 units/hour. In some embodiments, the basal parameter may be provided to an AID algorithm or process to determine a volume of insulin to inject into patient 150 via AID device 160 (such as 2.08 units every hour cycle, 1.04 units every half-hour cycle, and so on).

Figure 5:
FIG. 5 illustrates a third logic flow in accordance with the present disclosure

FIG. 5 illustrates an embodiment of a logic flow 500. Logic flow 500 may be representative of some or all of the operations executed by one or more embodiments described herein, such as devices of operating environments 100 and/or 200. In some embodiments, logic flow 500 may be representative of some or all of the operations of an insulin infusion process for determining a maximum additional insulin value according to some embodiments.

At block 502, logic flow 500 may determine a difference between a current A1C value and a target A1C value. For example, patient 150 may have a current A1C value of 9% (for instance, measured via a blood test and entered manually via computing device and/or accessed via electronic medical records of data sources 192*a-n*) and a target A1C of 7% for a current A1C—target A1C difference of 2 (or 2%). Logic flow 500 may determine a mean blood glucose difference based on the A1C difference at block 504. For example, insulin delivery application 140 may use Equation (3) to determine the mean blood glucose difference ($BG_{diff}$). Logic flow 500 may determine the additional insulin at block 506. For example, insulin delivery application 140 may use Equation (5) to determine $I_{add}$ based on $BG_{diff}$ and CF (determined using Equation (4)).

At block 508, logic flow 500 may set the total additional insulin as the maximum additional automated insulin delivery. For example, $I_{ADD}$ may be set as the maximum additional delivery of insulin allowed beyond the basal parameter that may be delivered by AID device 160 (for example, for bolus needs). Logic flow 500 may determine whether a maximum amount of insulin has been delivered at block 510. For example, at a delivery time or cycle t, insulin delivery application 140 may use Equation (6) to determine whether a maximum amount of insulin would be injected into patient 150 at time t. For example, in reference to Equation (6), if $\Sigma_{i=1}^{t} AID_{alg}(t) - basal(t) \le basal * t$ evaluates to true, then the maximum amount of insulin has not been injected into patient 150 and the $AID_{alg}(t)$ value may be used at block 512. Alternatively, in reference to Equation (6), if $\Sigma_{i=1}^{t} AID_{alg}(t) - basal(t) > basal * t$ evaluates to true, then the maximum amount of insulin has been injected into patient 150 and the basal amount of insulin b(t) is used as $I_{AID}(t)$ at block 514.

Figure 6:
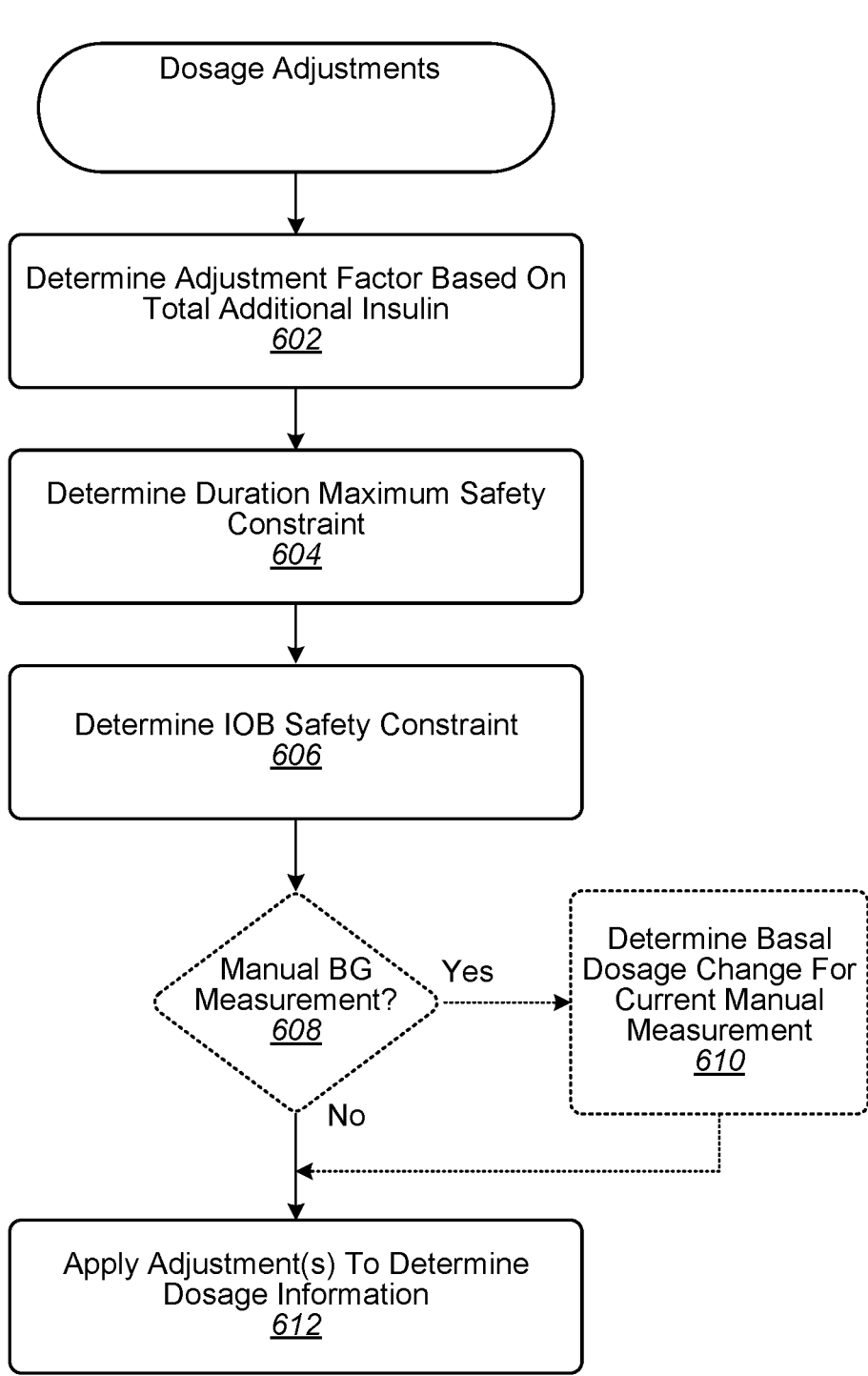
FIG. 6 illustrates a fourth logic flow in accordance with the present disclosure; and The drawings are not necessarily to scale. The drawings are merely representations, not intended to portray specific parameters of the disclosure. The drawings are intended to depict example embodiments of the disclosure, and therefore should not be considered as limiting in scope. In the drawings, like numbering represents like elements

FIG. 6 illustrates an embodiment of a logic flow 600. Logic flow 600 may be representative of some or all of the operations executed by one or more embodiments described herein, such as devices of operating environments 100 and/or 200. In some embodiments, logic flow 600 may be representative of some or all of the operations of an insulin infusion process for determining dosage adjustments according to some embodiments.

At block 602, logic flow 600 may determine an adjustment factor based on total additional insulin. For example, insulin delivery application 140 may determine $F_S$ based on Equation (7). In some embodiments, $F_S$ may be used to adjust (for example, relax) safety constraints used to determine an insulin delivery volume at a particular delivery cycle, for instance, via an AID algorithm.

Logic flow 600 may determine a duration maximum threshold at block 604. For example, insulin delivery application 140 may determine a duration maximum threshold (or integral delivery) safety constraint via Equation (8). In some embodiments, the duration maximum threshold may specify that the total insulin delivery for patient 150 during a certain duration (for example, 3 hours) cannot exceed a tunable factor (for instance, 9) times the basal parameter. At block 606, logic flow 600 may determine an IOB threshold. For example, insulin delivery application 140 may determine an IOB based on Equation (9). In exemplary embodiments, the IOB safety constraint may include determining insulin delivery in deviations from basal as a baseline.

At block 612, logic flow 600 may apply the dosage adjustments to determine dosage information. For example, insulin delivery application 140 may apply the safety constraints determined in blocks 604 and 606 to determine a dosage amount for an infusion cycle based, for instance, on application of an AID algorithm. The dosage amount may be administered to patient 150.

In some embodiments, logic flow 600 may be used to manage manual blood glucose (BG) measurements. For example, at block 608, logic flow 600 may determine whether manual BG measurements are being used by AID device 160 (for instance, fingerstick-based measurements). If manual BG measurements are being used, logic flow 600 may determine a basal dosage change for a current manual measurement at block 610. For example, insulin delivery application 140 may determine Δb(i), which represents a change in basal of patient 150 based on a current manual or fingerstick BG measurement, via Equation (10). In some embodiments, Δb(i) may be made asymmetric and/or dependent on the current blood glucose of patient 150, for example, based on Equation (12). In various embodiments, an adjustment based on Δb(i) may be used by logic flow 600 to apply adjustments to determine dosage information at block 612.

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or an entire item unless specifically stated to the contrary.

What is claimed is:

1. An apparatus, comprising:
at least one memory; and
logic coupled to the at least one memory, the logic to:
determine a basal parameter for a patient based on a type 2 diabetes (T2D) multiple daily injection (MDI) information of the patient, the basal parameter indicating a basal infusion rate, the MDI information comprising a multiple daily injection therapy specification describing a plurality of manual injections to be administered to the patient on a daily basis,
determine an additional insulin ($I_{add}$) value based on a mean blood glucose difference ($BG_{diff}$) information associated with the patient, the mean blood glucose difference ($BG_{diff}$) information determined based on a difference between a current glycated hemoglobin ($A1C_{current}$) level and a target glycated hemoglobin ($A1C_{target}$) level for the patient,
wherein the additional insulin ($I_{add}$) value is determined according to:

$$I_{add} = \frac{BG_{diff}}{CF} * x,$$

where x is a tunable cycle parameter configured to represent a number of cycles of insulin peak times per an infusion time period and CF is a correction factor
determine an insulin volume to infuse into the patient based on the basal parameter and the additional insulin ($I_{add}$) value, and
administer the insulin volume to the patient.

2. The apparatus of claim 1, the logic to determine the basal parameter according to:

$$TDI = \sum_{n=1}^{n_{max}} MDI_n,$$

and $$\text{basal parameter} = \frac{TDI}{t},$$

where t is an infusion time period and TDI is a total daily insulin.

3. The apparatus of claim 1, wherein the mean blood glucose difference ($BG_{diff}$) information is determined based on the equation $$A1C_{current} - A1C_{target} = (BG_{diff} + 68.8)/31.5.$$

4. The apparatus of claim 1,
wherein CF is determined according to:

$$CF = \frac{y}{z * \text{basal}},$$

where y is an insulin sensitivity factor, z is the infusion time period, and basal is a basal need of the patient in a time period defined by the infusion time period.

5. The apparatus of claim 1, the logic to adjust the insulin volume based on at least one safety constraint.

6. The apparatus of claim 5, the logic to determine the at least one safety constraint based on an adjustment factor ($F_S$) determined based on a total daily insulin (TDI) and the additional insulin ($I_{add}$) value according to:

$$F_s = 1 + \max\left(0, \frac{I_{add}}{TDI}\right).$$

7. The apparatus of claim 5, the at least one safety constraint comprising a duration maximum safety constraint indicating a maximum volume of insulin that may be infused into the patient during a duration.

8. The apparatus of claim 5, the at least one safety constraint comprising an insulin-on-board (IOB) safety constraint indicating deviations from basal infusion for the patient.

9. The apparatus of claim 1, the logic to determine the insulin volume using an automatic insulin delivery (AID) process based on continuous glucose measurement (CGM) information of the patient.

10. The apparatus of claim 1, the logic to determine the insulin volume using an automatic insulin delivery (AID) process using manual blood glucose measurement information of the patient.

11. The apparatus of claim 10, the logic to determine an adjustment ($\Delta$b(i)) in insulin delivery responsive to receiving the manual blood glucose measurement information for the patient, wherein the adjustment ($\Delta$b(i)) represents a change in basal insulin of the patient based on the manual blood glucose measurement information for the patient.

12. A method, comprising:

operatively coupling an automatic insulin delivery (AID) device to a patient;

performing, via a processor of a computing device operatively coupled to the AID device, an insulin infusion method by:

determining a basal parameter for the patient based on a type 2 diabetes (T2D) multiple daily injection (MDI) information of the patient, the basal parameter indicating a basal infusion rate, the MDI information comprising a multiple daily injection therapy specification describing a plurality of manual injections to be administered to the patient on a daily basis, determining an additional insulin ($I_{add}$) value based on a mean blood glucose difference ($BG_{diff}$) information associated with the patient, the mean blood glucose difference ($BG_{diff}$) information determined based on a difference between a current glycated hemoglobin ($A1C_{current}$) level and a target glycated hemoglobin ($A1C_{target}$) level for the patient, wherein the additional insulin ($I_{add}$) value is determined according to:

$$I_{add} = \frac{BG_{diff}}{CF} * x,$$

where x is a tunable cycle parameter configured to represent a number of cycles of insulin peak times per an infusion time period, where CF is a correction factor determined according to:

$$CF = \frac{y}{z * \text{basal}},$$

where y is an insulin sensitivity factor, z is the infusion time period, and basal is a basal need of the patient in a time period defined by the infusion time period, and determining an insulin volume to infuse into the patient based on the basal parameter and the additional insulin ($I_{add}$) value; and administering the insulin volume to the patient via the AID device.

13. The method of claim 12, comprising determining the mean blood glucose difference ($BG_{diff}$) information determined based on:

$$A1C_{current} - A1C_{target} = (BG_{diff} + 68.8)/31.5$$

where $A1C_{current}$ is the patient's current glycated hemoglobin level and $A1C_{target}$ is the patient's target glycated hemoglobin level.

14. The method of claim 12, comprising adjusting the insulin volume based on at least one safety constraint.

15. The method of claim 14, the at least one safety constraint comprising a duration maximum safety constraint indicating a maximum volume of insulin that may be infused into the patient during a duration.

16. The method of claim 14, the at least one safety constraint comprising an insulin-on-board (IOB) safety constraint indicating deviations from basal infusion for the patient.

17. The method of claim 12, comprising determining the insulin volume using an automatic insulin delivery (AID) process based on continuous glucose measurement (CGM) information of the patient.

18. The method of claim 12, comprising determining the insulin volume using an automatic insulin delivery (AID) process using manual blood glucose measurement information of the patient.

19. The method of claim 18, comprising determining an adjustment ($\Delta$b(i)) in insulin delivery responsive to receiving the manual blood glucose measurement information for the patient, wherein the adjustment ($\Delta$b(i)) represents a change in basal insulin of the patient based on the manual blood glucose measurement information for the patient.

* * * * *